United States Patent
Hobson et al.

(10) Patent No.: US 6,417,236 B1
(45) Date of Patent: Jul. 9, 2002

(54) ACTIVE TOPICAL SKIN PROTECTANTS USING HYBRID ORGANIC POLYSILSESQUIOXANE MATERIALS

(75) Inventors: Stephen T. Hobson, Belcamp; Ernest H. Braue, Whiteford, both of MD (US); Kenneth Shea, Irvine, CA (US)

(73) Assignees: The United States of America as represented by the Secretary of the Army, Washington, DC (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/872,097

(22) Filed: Jun. 1, 2001

Related U.S. Application Data

(60) Provisional application No. 60/209,337, filed on Jun. 2, 2000.

(51) Int. Cl.[7] ........................ A61K 31/02; A61K 31/08; A61K 47/00; A61K 7/42
(52) U.S. Cl. ..................... 514/759; 424/59; 514/723; 514/772; 514/789; 514/844; 514/845; 514/937; 514/939; 514/944
(58) Field of Search .................... 424/59; 514/723, 514/759, 772, 789, 844, 845, 937, 939, 944

(56) References Cited

U.S. PATENT DOCUMENTS

| | | | | |
|---|---|---|---|---|
| 4,649,037 A | 3/1987 | Marsh et al. | ............... | 423/338 |
| 5,607,979 A | 3/1997 | McCreery | ................... | 514/759 |
| 5,914,436 A | 6/1999 | Klabunde et al. | ........... | 588/205 |
| 5,990,373 A | 11/1999 | Klabunde | ................... | 588/200 |
| 6,057,488 A | 5/2000 | Koper et al. | ................ | 588/200 |
| 6,224,885 B1 | 5/2001 | Jenner | ........................ | 424/401 |

OTHER PUBLICATIONS

Smith, et al., Jrnl. of the American Acad. of Dermatology, Vo. 32, No. 5, part 1, May 1995, pp. 765–776, Sulfur mustard: Its continuing threat as a chemical warfare agent, the cutaneous lesions induced, progress in understanding its mechanism of action, its long–term health effectgs, and new developments for protection therapy.

Arroyo, et al., Jrnl. of Pharm. and Toxicol. Methods, vol. 33, No. 2, Apr. 1995, pp. 109–112, EPR/Spin–Label Technique as an Analytical Tool for Determining the Resistance of Reactive Topical Skin Protectants (rTSPs) to the Breakthrough of Vesicant Agents.

*Primary Examiner*—Shelley A. Dodson
(74) *Attorney, Agent, or Firm*—Elizabeth Arwine

(57) ABSTRACT

A topical skin protectant formulation containing a barrier cream and an active hybrid organic-inorganic polysilsesquioxane material for protecting warfighters and civilians against all types of harmful chemicals, specifically chemical warfare agents (CWA's). The topical skin protectant offers a barrier property and an active moiety that serves to neutralize chemical warfare agents into less toxic agents.

43 Claims, 2 Drawing Sheets

ACTIVE TOPICAL SKIN PROTECTANTS USING HYBRID ORGANIC POLYSILSESQUIOXANE MATERIALS

PRIORITY INFORMATION

This application claims the benefit of priority of U.S. Provisional Application No. 60/209,337 filed Jun. 2, 2000.

BACKGROUND OF THE INVENTION

1. Field of the Invention

This invention relates to active topical skin protectants. More specifically, the invention relates to an active barrier cream for protection against all types of harmful chemicals, specifically chemical warfare agents (CWA's). The active barrier cream is applied prior to exposure on the skin of persons at risk of exposure to harmful chemicals to provide a protective barrier for the skin. The active barrier cream chemically or physically reacts with harmful chemicals such as CWA's (vesicants and nerve agents) to neutralize these harmful chemicals while the barrier properties of the cream prevent penetration of harmful chemicals through the cream to the skin.

2. Description of Related Art

The concept of applying a topical protectant to vulnerable skin surfaces before entry into a chemical combat arena has been proposed as a protective measure against percutaneous CWA toxicity since the first use of CWA's in World War I. The protectant was applied to vulnerable skin surfaces prior to entry into a chemical combat area. Topical protectants should augment the protection afforded by the protective overgarments and/or redefine the circumstances requiring mission oriented protective posture (MOPP) levels. The rapid action of vesicating agents, also known as blistering agents, such as sulfur mustard (HD) and lewisite (L), require a pre-exposure skin protection system or a contamination avoidance approach that may preclude the percutaneous toxicity of these agents. These approaches also reduce the risk of exposure to organophosphorus (OP) chemical agents (nerve agents) that are lethal in droplet amounts.

An organic molecule, S-330, that reacts with CWA's was incorporated into a product and fielded as the M-5 ointment kit at the end of World War II (Formula 1).

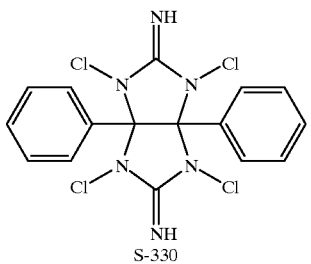

Formula 1. S-330

However, the unacceptable barrier properties and the undesirable cosmetic properties (specifically foul odor and sticky texture) caused a recall of this product.

Two non-active topical skin protectant (TSP) formulations were developed at the United States Army Medical Research Institute of Chemical Defense (USAMRICD) and were transferred to advanced development following a Milestone Zero (MS0) Review in October 1990. The timeline of the approval of the TSP continued with MSI in 1993, a Investigational New Drug (IND) filed with the FDA in 1994, MSII in 1995, and culminated with New Drug Application (NDA) approval in February, 2000. Upon approval by the FDA, the TSP was designated Skin Exposure Reduction Paste Against Chemical Warfare Agents (SERPACWA). SERPACWA is a 50:50 (wt/wt) mixture of perfluoropolyether oil (Fomblin® Y25 from Ausimont) and poly(tetrafluoroethylene)(polymist® F5a powder from Ausimont). The formulation described in McCreery U.S. Pat. No. 5,607,979 is directed to a topical skin protectant cream that acts as a barrier to CWA's.

Although SERPACWA extends the protection afforded by MOPP and allows a longer window for decontamination, it does not completely remove the possibility for contamination because the CWA is not neutralized. To avoid contamination of other areas of the battlefield and to preclude the future percutaneous absorption of the CWA, decontamination is still required. Furthermore, although the McCreery formulation provides excellent protection against GD and HD liquid, its protection against HD vapor is minimal.

To overcome these deficiencies, there is a need for a new TSP that contains an active component. This active Topical Skin Protectant (active TSP) was developed within the following criteria. First, the active TSP should neutralize CWA's including but not limited to sulfur mustard (HD), soman (GD), and VX. Second, the barrier properties of the TSP should be maintained or increased. Third, the protection against HD vapor should increase. And fourth, the cosmetic characteristics (i. e. odor, texture) of the TSP should be maintained.

This invention meets the above criteria and solves the problems associated with the past TSP's by providing an active topical skin protectant that increases effectiveness of the TSP barrier quality and neutralizes CWA's into less harmful products.

It is therefore, an objective of the present invention to provide an active topical skin protectant that prevents the percutaneous absorption of CWA's and converts these toxic materials into less harmful products.

It is a further objective of the present invention to provide an active topical skin protectant that maintains desirable cosmetic properties making it acceptable to the user. Specifically, the active TSP should not be sticky, should be without offensive odor, and should be nonirritating to the skin.

It is still a further object of the invention to provide an active topical skin protectant that is practical for field operations. Specifically, the active TSP should have a stable shelf life, should not be easily washed off with water, and should not react with insecticides or camouflage paint.

SUMMARY OF THE INVENTION

A topical skin protectant formulation for neutralizing chemical warfare agents into less toxic products comprising: a barrier base cream and one or more active moieties. The base cream comprises poly(tetrafluoroethylene) resins dispersed in perfluorinated polyether oils. The active moieties that have been found to be effective with the base cream are listed in Table 1. The active barrier cream is applied to the skin prior to exposure of persons at risk of exposure to harmful chemicals to provide an active barrier to protect the skin. The active barrier cream chemically or physically reacts with harmful chemicals such as CWA's to neutralize these harmful chemicals while the barrier properties of the cream prevent penetration of harmful chemicals through the cream to the skin.

DETAILED DESCRIPTION

Candidate Active Moieties

Figure 1:
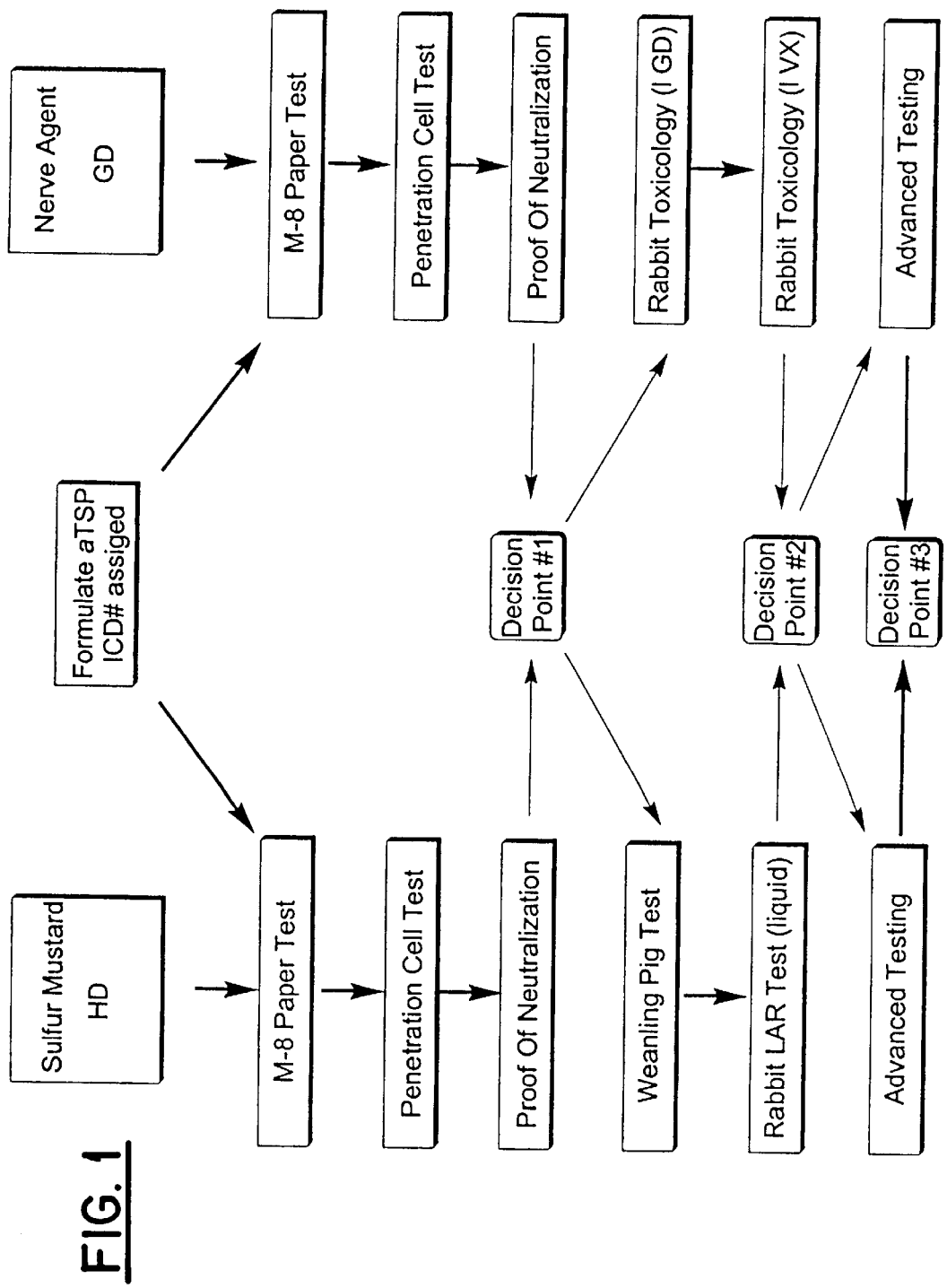
FIG. 1 is a flow diagram of the active TSP Decision Tree Network for efficacy evaluation.

The types of materials that decontaminate harmful agents use two main modes of action: elimination or hydrolysis.

However, selection of the active materials is restricted by operating criteria. Thus, the active moiety must not irritate the skin, react with insecticides or camouflage paints, or be unstable. This restriction eliminates many of the most active species. Furthermore, the active moiety must be incorporated into a highly fluorinated environment that is not amenable to many reaction pathways.

Table 1 is a list of active moieties that are acceptable for use in the present invention.

TABLE 1

LIST OF ACTIVE HYBRID ORGANIC-INORGANIC POLYSILSESQUIOXANES FOR ACTIVE TOPICAL SKIN PROTECTANTS AND EXAMPLE FORMULATONS

Example Formulations

| ICD # | Active Moiety | Wt % Active | Wt % PFPE | Wt % PTFE |
|---|---|---|---|---|
| 3172 | 60% PhB/40% MPTES | 4 | 58 | 38 |
| 3173 | 40% PhB/60% MPTES | 4 | 58 | 38 |
| 3189 | 20% PhB/80% MPTES | 4 | 58 | 38 |
| 3190 | 60% PhB/40% TESDS | 5 | 57 | 38 |
| 3191 | 40% PhB/60% TESDS | 4 | 58 | 38 |
| 3192 | 20% PhB80% TESDS | 4 | 58 | 38 |
| 3305 | 60% PhB/40% MPTES | 3 | 57 | 40 |
| 3314 | 60% PhB/40% MPTES | 4 | 96 | |
| 3450 | 100% PhB | 5 | 51 | 44 |
| 3530 | 60% PhB/40% TESDS | 1 | 50 | 49 |
| 3531 | 40% PhB 60%/TESDS | 1 | 50 | 49 |
| 3532 | 20% PhB/80% TESDS | 1 | 50 | 49 |
| 3533 | Silica Gel | 2.5 | 50 | 47.5 |
| 3548 | 100% PhB/THF | 5 | 51 | 44 |
| 3549 | 100% PhB/ethanol (3540) | 5 | 51 | 44 |
| 3550 | 60% PhB/40% MPTES (3541) | 5 | 51 | 44 |
| 3551 | 60% PhB/40% MPTES (3542) | 5 | 51 | 44 |
| 3552 | 60% PhB/40% MPTES (3543) | 5 | 51 | 44 |

Abbreviations:
PTFE: poly(tetrafluoroethylene)available as F5A powder from Ausimont, Morristown, NJ
PFPE: perfluoropolyether available as FOMBLIM ™ Y25 oil from Ausimont, Morristown, NJ
PhB 1,4-triethoxysilylbenzene
MPTES mercaptopropyltriethoxysilane (3-triethoxysilyl-propane-1-thiol)
TESDS 3,3'-triethoxysilylpropyl disulfide (1-triethoxysilyl-3-(3-triethoxysilylpropyldisulfanyl)-propane)
THF tetrahydrofuran
EtOH ethanol
*Silica gel SiO$_2$ Aldrich 70–230 mesh, 60 A, 500 m$^2$/g, #28862–4

Two monomers listed above are organic-bridged bistriethoxysilyl compounds (MPTES, PhB) prepared in the laboratory of Ken Shea at the University of California on Mar. 30, 2001 (Provisional Patent Application No. 60/280, 711).

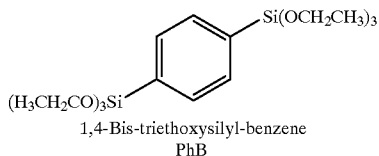
1,4-Bis-triethoxysilyl-benzene
PhB

-continued

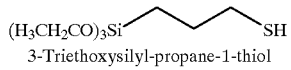
3-Triethoxysilyl-propane-1-thiol
MPTES

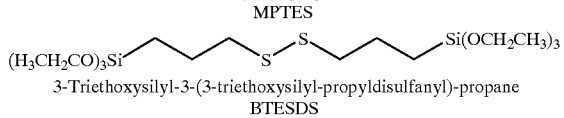
3-Triethoxysilyl-3-(3-triethoxysilyl-propyldisulfanyl)-propane
BTESDS

Monomers used in the synthesis of bridged polysilsesquioxanes.

Chemical structures for the bridged polysilsesquioxanes are below:

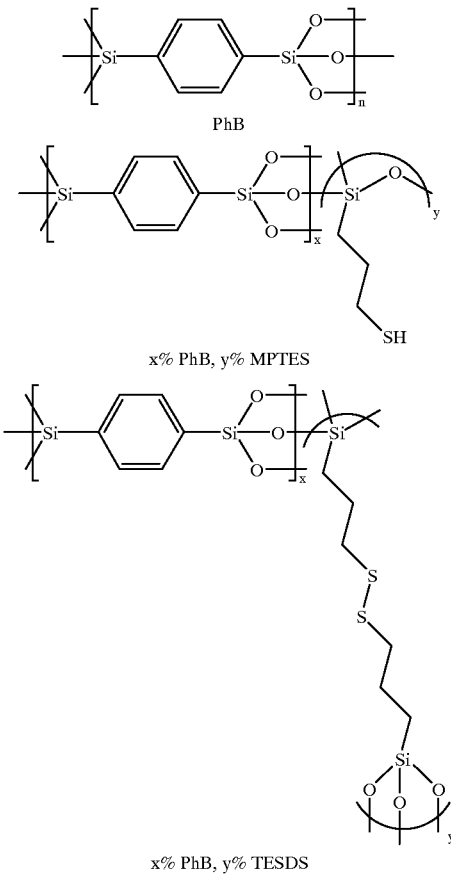

Structures of bridged polysilsesquioxanes incorporated into active TSPs

All active moieties listed above are useful for both liquid and vapor challenges. The amount of each varies with each formulation. The object is to optimize the quantity of active moiety in the base cream without losing the barrier properties of the base cream. The amount of active moiety can vary from about 1–20%. The amount of perfluorinated polyether oil can vary from about 40 to 60%. The amount of poly (tetrafluoroethylene) can vary from about 30 to 50%. One criterion for selection of the active materials is increased efficacy against HD and/or GD vapor. Many formulations have significantly (P=0.05) increased protection compared to SERPACWA (ICD 3004) in the penetration cell model against HD and GD respectively. The best candidate compound listed in Table 1 for HD is ICD3553 and for GD is ICD3362.

The bridged polysilsesquioxane must also be incorporated into the TSP matrix without degradation of the barrier properties. These materials were incorporated into the cream as solids. Typically, they are dispersed into the perfluorinated oil followed by sequential addition of the appropriate amount of F5A polytetrafluoroethylene.

SERPACWA (ICD3004) consists of fine particles of poly (tetrafluoroethylene) resin dispersed in perfluorinated polyether oil. The excellent barrier properties of this high molecular weight polymer formulation are related to the low solubility of most materials in it. Only highly fluorinated solvents like Freon® have been observed to show appreciable solubility. This aprotic non-polar polymer mixture provides a unique. medium for active moieties of the invention. Reaction mechanisms that do not involve charged transition states should be favored in this chemical environment.

Base creams formed from about 35–50% fine particulates of certain poly(tetrafluoroethylene) PTFE resins dispersed in perfluorinated polyether oils (PFPE) having viscosities from about 20 cSt to about 500 cSt afford good protection against chemical warfare agents such as HD, L, sulfur mustard/Lewisite mixtures (HL), pinacolyl methylphosphonofluoridate (soman or GD), thickened soman (TGD) and O-ethyl S-(2-diisopropylaminoethyl)methylphosphonothiolate (VX). PTFE and PFPE are available commercially from Ausimont (Morristown, N.J.) and Dupont (Wilmington, Del.).

The base creams used in the invention are suspensions of 35–50% finely divided PTFE having a surface area below about 6 $m^2/g$ in a perfluorinated polyether base oil prepared from perfluoropropylene oxide, which has a viscosity between about 20 and about 500 cSt. More preferred compositions comprise from about 35% to about 50% of finely divided PTFE having an average particle size from about 0.1 $\mu$m to about 10 $\mu$m and a surface area below about 4 $m^2/g$ in a perfluorinated polyether base oil from 40% to 60% having a viscosity between about 20 and about 500 cSt.

Suitable perfluorinated polyether oils are Fomblin® HC- and Y-oils (Ausmont) and Krytox.® oils (Dupont). The Fomblin® oils are mixtures of linear polymers based on perfluoropropylene oxide having the following chain structure: $CF_3—[(OCF(CF_3)CF_2)_n—(OCF_2CF_2)_m]OCF_3$. The Krytox® oils are mixtures of linear polymers also based on perfluoropropylene oxide and have the chemical structure $F—[(CF(CF_3)CF_2O)]_m CF_2CF_3$. Fomblin® Z oils having the formula: $CF_3. [(OCF_2CF_2)_n—(OCF_2)_m]—OCF_3$, may also be useful in the practice of the invention. The indices n and m indicate the average number of repeating polymeric subunits in the oil molecules. The oils may have a viscosity of about 20 cSt to about 500 cSt or more. The creams were generally prepared according to U.S. Pat. No. 5,607,979, incorporated herein in its entirety.

Other additives to the base cream are water and surfactant and other chemical necessary to maintain activity (see Table 1). The surfactant facilitates the mixing of the water with the base cream. An example of a typical surfactant is perfluoropolyalkylether (Krytox® CAS # 60164-51-4 from Dupont). Additional materials may also be incorporated as long as they do not reduce effectiveness of the topical protectant, such as stabilizers, camouflage paints, and sunscreens.

A further understanding of the composition of the topical protectant of the invention can be obtained by reference to certain specific example formulations set forth in Table 1. These examples are provided herein for purposes of illustration only and are not intended to be limiting. Many active moieties require the presence of water as a reagent for the hydrolysis of HD and GD. The active moieties that react by a hydrolysis mechanism require the presence of water. When the topical protectant is applied to the skin of a user, moisture in the form of perspiration may also aid in the hydrolysis of HD and GD. The addition of perfluorinated polyether surfactants to the base cream facilitates the addition of water.

Temperature and mixing sheer should be monitored to maintain the base cream at the desired consistency and quality. The active TSPs are typically prepared at ambient temperature using mechanical mixing. Depending on the oxygen sensitivity of the active material, some of the bridged polysilsesquioxanes may be added to the perfluorinated oil under an inert (i. e. nitrogen) atmosphere. Mixing times of 10–20 minutes are usually sufficient for dispersal of bridged polysilsesquioxanes into the SERPACWA matrix. A typical procedure for the preparation of an active aTSP with a bridge polysilsesquioxane is presented below:

In a polypropylene container is added the appropriate amount of bridged polysilsesquioxane (1–3% by weight) and Y25 (50–55% by weight) perfluorinated oil. The suspension is mixed either with a mechanical stirrer at ambient temperature for 5 to 15 minutes or with a magnetic stirrer for 12 to 24 hours. To the suspension is added F5A poly (tetrafluoroethylene) in three portions with vigorous mechanical stirring for 5 to 10 minutes between each addition. After the final addition, the container is tightly capped and sealed with Parafilm®.

Multilayer Approach

Although an active TSP can be generally the application of a powder that is a POM/RNP sprinkled on the skin, or an active moiety in a base cream wherein the cream is spread on the skin, a multilayering approach can also be used. The multilayer approach would be to use the active TSP as the first layer and a solid active moiety powder as the second layer. The second layer would be a thin coating of the solid active moiety powder sprinkled over the active TSP cream. This approach would provide a concentrated decontamination material at the surface of the barrier cream, which would accelerate the neutralization process of CWA's coming in contact with the surface. Alternatively, the first layer can be a thin coating of the solid active moiety powder followed by a second layer of the active TSP.

Testing

Evaluation of formulations was conducted with a decision tree network (DTN) that describes the path that active TSPs follow during evaluation (FIG. 1).

The DTN is divided into two pathways: one for vesicants and the other for nerve agents. Within these pathways, there are three blocks each with a decision point. The first block consists of a series of three mechanical (in vitro) modules used to determine the initial efficacy of candidate formulations and to eliminate non-effective candidates before animal testing, the second block consists of in vivo modules and the third block consists of an advanced animal module to determine the influence of time, water and interactions with other products.

The M8 paper test is used to evaluate the barrier resistance of liquid CWA challenges, including HD, pinacolyl methylphosphonofluoridate (soman, GD), and O-ethyl S-(2-diisopropylaminoethyl) methylphosphonothioate (VX). In this test a 0.15 mm layer of active TSP is placed over a well-defined area of M8 chemical detection paper and challenged with an 8 $\mu$l droplet of CWA. When agent penetrates the active TSP barrier and reaches the M8 paper, a colored spot develops on the paper. The test assemblies are observed for 6 hr and the breakthrough time is reported for each sample. Nine replicates are run for each test, and a standard reference compound is included each day for quality control.

The penetration cell test is used to evaluate the barrier properties against both liquid and vapor CWA challenges (Braue, E. H. Jr. *Journal of applied Toxicology*, 1999, 19(S), S47–S53). In this test, the lower half of a Reifenrath diffusion cell (Reifenrath Consulting and Research, Richmond, Calif.) is used. A 0.15 mm thick layer of active TSP is supported by nitrocellulose paper on top of the cell. The active TSP layer is challenged with a 10 µl liquid droplet of HD or an 8 µl droplet of GD, or a saturated vapor cup of HD or GD. Breakthrough of CWA into the lower chamber of the diffusion cell is monitored using a miniature continuous air monitoring system (MINICAMS, CMS Research, Birmingham, Ala.). This system has been automated to allow continuous monitoring of five cells in a 40-min cycle. The test runs for 20 hr and the accumulated amounts of agent that break through the active TSP barrier are calculated. From these data, we obtained two values: the cumulative amount of CWA that penetrates through the active TSP, and the time at which a "breakthrough" occurs. We defined "breakthrough" values at the minimum amount of HD (1000 ng) and GD (1000 ng) that results in a physiological response. Minimal amount of HD for vesication =1000 ng. See F. R. Sidell, J. S. Urbanetti, W. J. Smith, and C. G. Hurst in *Textbook of Military Medicine, Medical Aspects of Chemical and Biological Warfare*, edited by F. R. Sidell, E. T.Takafuji, and D. R. Franz (Office of the Surgeon General at TMM Publications, Washington, D. C. 1997) p 201. $LD_{50}$ for soman (GD) =350 mg/70 kg man. See F. R. Sidell in *Textbook of Military Medicine, Medical Aspects of Chemical and Biological Warfare*, edited by F. R. Sidell, E. T.Takafuji, and D. R. Franz (Office of the Surgeon General at TMM Publications, Washington, D. C. 1997) p 141. These two values allow us to rank the active TSP formulations and to select the appropriate component for advanced development.

The proof-of-neutralization test is used to verify that active TSP formulations actually neutralize CWAs into less toxic materials. This test uses the headspace solid phase microextraction (HS-SPME) technique for the collection of CWAs. Samples collected on the extraction filament are analyzed by gas chromatography/mass spectroscopy. 100 mg of active TSP formulation are challenged with 0.1 µl of neat CWA (HD, GD, or VX) in a small vial. The headspace above the mixture is sampled periodically to determine the amount of CWA remaining in the flask. Efficacy is determined by the % loss of CWA. Other analytical techniques such as Nuclear Magnetic Resonance (NMR) and Fourier-Transform Infrared Spectrometry (FTIR) have also been used in this module.

Formulations that pass this initial set of screens are moved into the second phase of testing using animal models. The weanling pig test for HD vapor evaluates a 0.10 to 0.20 mm thick layer of active TSP spread on the depilated dorsa. The standard saturated vapor cup is used for a 15–60 min challenge. The effectiveness of the active TSP is determined by measuring the degree of erythema that developed on the skin exposure site. Erythema is measured objectively using a reflectance calorimeter (see Braue, E. H. Jr. *Journal of applied Toxicology*, 1999, 19(S), S47–S53)

The rabbit lesion area ratio (LAR) test is used to evaluate a challenge by HD liquid. In this test, a 0.10 mm layer of active TSP spread on the clipped dorsa is challenged with 1.0 µl of liquid HD. The effectiveness of the active TSP is determined by measuring the lesion areas of protected and non-protected sites.

The rabbit acetyl cholinesterase (AChE) inhibition test is performed by applying a 0.10 mm thick layer of active TSP on the clipped dorsa of rabbit followed by a fixed dose of GD (1 $LD_{50}$), TGD (1 $LD_{50}$), or VX (20 $LD_{50}$). The effectiveness of the active TSP is determined by lethality and by measuring the erythrocyte acetyl cholinesterase activity 0.5, 1, 2, and 24 hr following exposure.

Candidate formulations that pass the in vivo test modules move into advanced animal testing. These tests are similar to the initial animal tests with the addition of stresses for wear-time and washing with water. Interactions with other products that a soldier might use are also evaluated. These products include camouflage paints, sunscreens and insecticides.

Results

Both the phenyl-bridged polysilsesquioxane (PhB) and the phenyl-bridged/bistriethyoxysilylpropyldisulfide (PhB/BTESPDS) are effective active moieties reducing the amount of HD vapor by ~98% relative to the TSP alone. Although the exact mechanism for HD neutralization is not clear, the HD may react by either hydrolysis or dehydrohalogenation (Scheme 1).

Scheme 1.
Possible neutralization reactions of polysilsesquioxanes with HD.

$$HO\diagup\diagdown S\diagup\diagdown OH \underset{hydrolysis}{\overset{H_2O}{\longleftarrow}} Cl\diagup\diagdown S\diagup\diagdown Cl \underset{dehydrohalogenation}{\overset{\overset{OH}{|}\atop\underset{R}{\overset{|}{-(Si)-}}}{\longrightarrow}} Cl\diagup\diagdown S\diagdown\!\!=$$
1      HD      2

The hydrolysis of HD to thiodiglycol 1 perhaps is due to adventitious water trapped on the polysilsesquioxane surface or in the internal pore structure. Since these materials have high surface areas (up to 850 m$^2$/g), this reaction may be facilitated by the physical or chemical adsorption of the HD into the polysilsesquioxane. This adsorption should be energetically favorable due to the hydrophobic nature of the hybrid organic-inorganic polysilsesquioxanes. On the other hand, since these materials are not completely condensed (~80% condensation as determined by $^{29}$Si SS-NMR) it is possible that the residual silanols (RSiOH) will act as an acid catalyst for the dehydrohalogenation reaction giving vinylsulfide 2. This hypothesis is supported by the high activity of silica gel (SiO$_2$, ICD 3533).

Against GD vapor, the most effective bridged polysilsesquioxanes were the phenyl-bridged polysilsesquioxane (PhB) that reduced the amount of GD by 88% compared to TSP alone. The most likely mechanism for the neutralization of GD is hydrolysis (Scheme 2).

Scheme 2.
Hydrolyses of soman (GD) with bridged polysilsesquioxanes.

All active TSPs that have shown efficacy against GD contain water, and the products from the GD simulant, diisopropylfluorophosphate, (DFP), have FT-IR and $^{31}P$ NMR spectra that are consistent with hydrolysis. Adventitious adsorbed water on the surface of the bridged polysilsesquioxanes or in the internal surface structure may act as a reagent for this hydrolysis. Furthermore, a physical or chemical adsorption of the GD into the relatively hydrophobic polysilsesquioxane matrix may also play a role (vide infra).

The increase in protection for the bridged polysilsesquioxane was impressive against GD vapor as seen by the increase in the time for 1000 ng of GD vapor to penetrate the active TSP as compared to SERPACWA (ICD 3004) (Chart 1).

Chart 1. Time for 1000 ng GD to penetrate aTSPs with bridged polysilsesquioxane.

This protection is also evident in a comparison of the cumulative amount of GD vapor that penetrates the active TSP over 20 hours in comparison to SERPACWA (ICD3004) (Chart 2).

Chart 2. Cumulative amount of GD vapor through aTSP over 20 hr.

Formulations ICD 3530, 3548, and 3450 show the greatest protection against GD vapor reducing the amount of GD by 80, 83, and 88% respectively and all have significantly (P=0.05) increased protection compared to SERPACWA (ICD 3004) in the penetration cell model against GD. The importance of the organic bridging group is also obvious by comparing the 22% reduction of the amount of GD penetration for silica gel ($SiO_2$, ICD 3533) and the ~90% reduction for the hybrid organic-inorganic polysilsesquioxanes ~90% (ICD 3450, PhB). Apparently, the organic bridge is a necessary to for the increased protection and for the neutralization of the organophosphate.

The increase in protection for the bridged polysilsesquioxanes was also remarkable against HD vapor as demonstrated in the increase in the time needed for 1000 ng of HD vapor to penetrate the active TSP as compared to SERPACWA (ICD 3004) (Chart 3).

Chart 3. Time for 1000 ng HD to penetrate active TSPs containing bridged polysilsesquioxane A comparison of the cumulative amount of HD vapor that penetrates the active TSP over 20 hours also shows the increase in protection (Chart 4).

HD(v) cumulative amount pen cell

Chart 4. Cumulative amount of HD vapor through aTSP over 20 hr.

As clearly seen in Chart 4, the majority of formulations have shown outstanding protection against HD vapor in the penetration cell model. In fact, as few as 52 ng of HD vapor penetrated through the active TSP over 20 hours. All but one formulation show the same protection or significantly better (P=0.05) protection against HD vapor compared to ICD 3004 in the penetration cell model.

Figure 2:
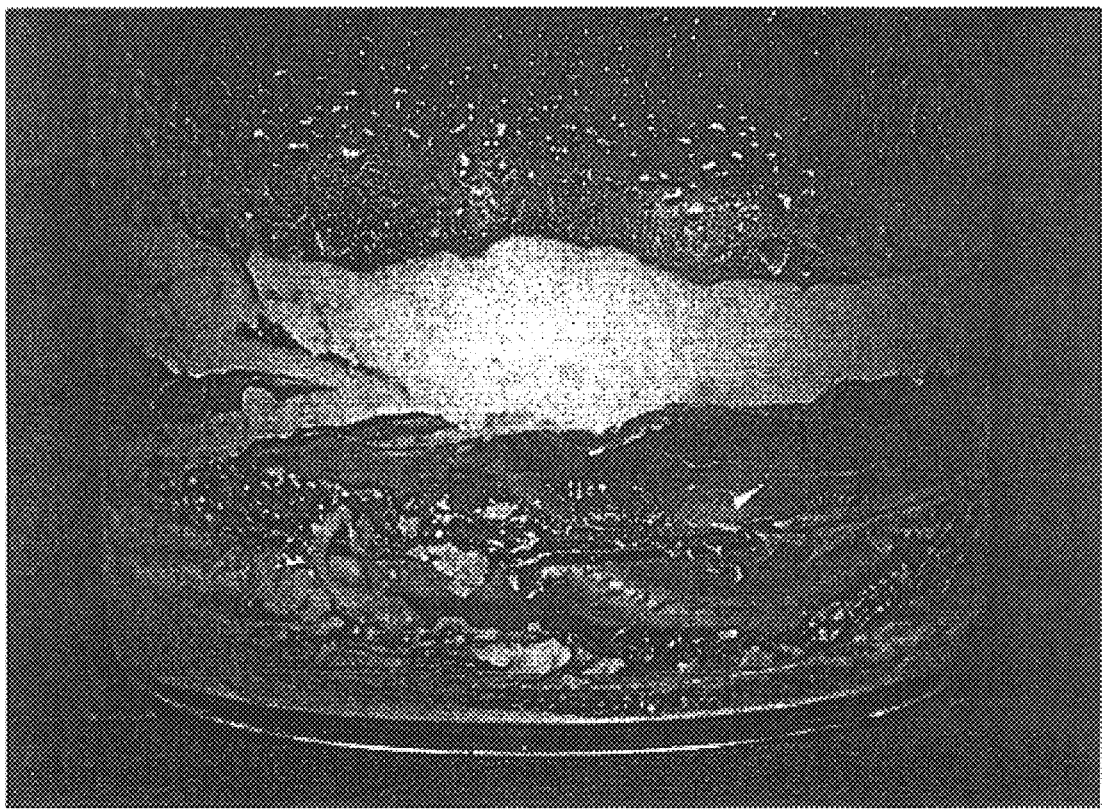
FIG. 2 is a picture of bridged polysilsesquioxanes/Y25 after exposure to DFP (t=20 hr). Examination of $^{31}$P NMR revealed no signals from hydrolyzed or native DFP.

In the proof of neutralization model, ICD 3450 (PhB polysilsesquioxanes) was tested in the head-space solid phase micro-extraction gas chromatography/mass spectrometry (HS-SPME/GC-MS) test against HD, GD, and VX liquid. In these tests, the active TSPs only showed significant efficacy against HD liquid (46±17%). The neutralization of diisopropylfluorophosphonate (DFP) was monitored via $^{31}$P NMR in the PFPE oil. After 20 hours, no perceptible signal from DFP was seen in the $^{31}$P NMR. An examination of the vial containing the bridged polysilsesquioxane indicated that physical removal of the DPF might have occurred (FIG. 2). Furthermore, examination of $^{31}$P NMR revealed no signals from hydrolyzed or native DFP.

Despite the excellent performance of the active TSPs containing bridged polysilsesquioxanes in the penetration cell models, the results from the weanling pig model were more varied (Chart 5)

HD(v) Weanling Pig model

Chart 5. Results of active TSPs containing bridged polysilsesquioxanes.

The active TSPs containing bridged polysilsesquioxanes reduced the cumulative amount of HD vapor in the penetration cell by 88–96% (Chart 4). The recorded erythema from HD vapor in these active TSPs, however, is only slightly decreased or actually increased above control in the in vivo test. The only exception was seen when the thickness of the active TSP was increased from 0.1 mm to 0.2 mm. We have seen similar trends with other compounds and have four possible explanations. First, the skin is occluded by the aTSP, increasing agent penetration and thus the observed erythema. Second, the skin may be sensitized by the aTSP, and thus the small amount of HD vapor that penetrates the skin results in greater erythema. Third, the skin may be irritated by the reaction products. Fourth, agent may penetrate the aTSP during exposure and not be completely removed by the cleaning procedure.

Having now fully described the invention, it will be apparent to one of ordinary skill in the art that many changes and modifications can be made thereto without departing from the spirit or scope of the invention as set forth herein.

What is claimed is:

1. A topical skin protectant formulation for neutralizing chemical warfare agents into less toxic products comprising: a barrier base cream; and one or more hybrid organic-inorganic polysilsesquioxane as an active moiety.

2. The topical skin protectant formulation of claim 1, wherein the base cream comprises poly(tetrafluoroethylene) resins dispersed in perfluorinated polyether oils.

3. The topical skin protectant formulation of claim 1, wherein said hybrid organic-inorganic polysilsesquioxanes is selected from the group consisting of:
   a) bridged polysilsesquioxane prepared from 60% 1,4-Bis-triethoxysilyl-benzene/40% 3-Triethoxysilyl-propane-1-thiol;
   b) hybrid organic-inorganic polysilsesquioxane prepared from 40% 1,4-Bis-triethoxysilyl-benzene/60% 3-Triethoxysilyl-propane-1-thiol;
   c) hybrid organic-inorganic polysilsesquioxane prepared from 20% 1,4-Bis-triethoxysilyl-benzene/80% 3-Triethoxysilyl-propane-1-thiol;
   d) hybrid organic-inorganic polysilsesquioxane prepared from 60% 1,4-Bis-triethoxysilyl-benzene/40% 1-Triethoxysilyl-3-(3-triethoxysilyl-propyldisulfanyl)-propane;
   e) hybrid organic-inorganic polysilsesquioxane prepared from 40% 1,4-Bis-triethoxysilyl-benzene/60% 1-Triethoxysilyl-3-(3-triethoxysilyl-propyldisulfanyl)-propane;
   f) hybrid organic-inorganic polysilsesquioxane prepared from 20% 1,4-Bis-triethoxysilyl-benzene/80% 1-Triethoxysilyl-3-(3-triethoxysilyl-propyldisulfanyl)-propane;
   g) hybrid organic-inorganic polysilsesquioxane prepared from 1,4-Bis-triethoxysilyl-benzene in tetrahydrofuran; and
   h) hybrid organic-inorganic polysilsesquioxane prepared from 1,4-Bis-triethoxysilyl-benzene in ethanol.

4. The topical skin protectant formulation of claim 1, wherein said hybrid organic-inorganic polysilsesquioxanes comprises monomers and wherein said monomers are 1,4-Bis-triethoxysilyl-benzene, 3-Triethoxysilyl-propane-1-thiol or 1-Triethoxysilyl-3-(3-triethoxysilyl-propyldisulfanyl)-propane.

5. A topical skin protectant formulation for neutralizing chemical warfare agents into less toxic products comprising:
   a) a barrier base cream, said barrier base cream comprising poly(tetrafluoroethylene) resins dispersed in perfluorinated polyether oils; and b) one or more active moieties comprising one or more hybrid organic-inorganic polysilsesquioxanes.

6. The topical skin protectant formulation of claim 5, further comprising one or more additives.

7. The topical skin protectant formulation of claim 6, wherein said additives comprise one or more of water, surfactants, stabilizers, camouflage paints, and sunscreens.

8. A topical skin protectant formulation for neutralizing chemical warfare agents into less toxic products comprising:
   a) a barrier base cream, said barrier base cream comprising poly(tetrafluoroethylene) resins dispersed in perfluorinated polyether oils;
   b) one or more active moieties comprising hybrid organic-inorganic polysilsesquioxanes selected from the group consisting of hybrid organic-inorganic polysilsesquioxane prepared from a) 60% 1,4-Bis-triethoxysilyl-benzene, 40% 3-Triethoxysilyl-propane-1-thiol, b) hybrid organic-inorganic polysilsesquioxane prepared from 40% 1,4-Bis-triethoxysilyl-benzene, 60% 3-Triethoxysilyl-propane-1-thiol,
   c) hybrid organic-inorganic polysilsesquioxane prepared from 20% 1,4-Bis-triethoxysilyl-benzene, 80% 3-Triethoxysilyl-propane-1-thiol,
   d) hybrid organic-inorganic polysilsesquioxane prepared from 60% 1,4-Bis-triethoxysilyl-benzene, 40% 1-Triethoxysilyl-3-(3-triethoxysilyl-propyldisulfanyl)-propane,
   e) hybrid organic-inorganic polysilsesquioxane prepared from 40% 1,4-Bis-triethoxysilyl-benzene, 60% 1-Triethoxysilyl-3-(3-triethoxysilyl-propyldisulfanyl)-propane,
   f) hybrid organic-inorganic polysilsesquioxane prepared from 20% 1,4-Bis-triethoxysilyl-benzene, 80% 1-Triethoxysilyl-3-(3-triethoxysilyl-propyldisulfanyl)-propane,
   g) hybrid organic-inorganic polysilsesquioxane prepared from 1,4-Bis-triethoxysilyl-benzene in THF,
   h) and Hybrid organic-inorganic polysilsesquioxane prepared from 1,4-Bis-triethoxysilyl-benzene in EtOH; and
   i) one or more additives.

9. The topical skin protectant formulation of claim 8, wherein said additives comprise one or more of water, surfactants, stabilizers, camouflage paints, and sunscreens.

10. A topical skin protectant system comprising:
    a) a topical skin protectant formulation for neutralizing chemical warfare agents into less toxic products comprising a barrier cream and one or more active moieties, said active moieties comprising hybrid organic-inorganic polysilsesquioxanes;
    b) a second formulation for applying a thin solid active moiety powder on top or below said topical skin protectant formulation comprising one or more hybrid organic-inorganic polysilsesquioxanes.

11. The topical skin protectant system of claim 10 wherein said one or more active moieties in the topical skin protectant formulation and in the solid active moiety powder is an hybrid organic-inorganic polysilsesquioxanes selected from the group consisting of:
    a) hybrid organic-inorganic polysilsesquioxane prepared from 60% 1,4-Bis-triethoxysilyl-benzene and 40% 3-Triethoxysilyl-propane-1-thiol;
    b) hybrid organic-inorganic polysilsesquioxane prepared from 40% 1,4-Bis-triethoxysilyl-benzene and 60% 3-Triethoxysilyl-propane-1-thiol;
    c) hybrid organic-inorganic polysilsesquioxane prepared from 20% 1,4-Bis-triethoxysilyl-benzene and 80% 3-Triethoxysilyl-propane-1-thiol;
    d) hybrid organic-inorganic polysilsesquioxane prepared from 60% 1,4-Bis-triethoxysilyl-benzene and 40% 1-Triethoxysilyl-3-(3-triethoxysilyl-propyldisulfanyl)-propane;
    e) hybrid organic-inorganic polysilsesquioxane prepared from 40% 1,4-Bis-triethoxysilyl-benzene and 60% 1-Triethoxysilyl-3-(3-triethoxysilyl-propyldisulfanyl)-propane;
    f) hybrid organic-inorganic polysilsesquioxane prepared from 20% 1,4-Bis-triethoxysilyl-benzene and 80% 1-Triethoxysilyl-3-(3-triethoxysilyl-propyldisulfanyl)-propane;
    g) hybrid organic-inorganic polysilsesquioxane prepared from 1,4-Bis-triethoxysilyl-benzene in tetrahydrofuran; and
    h) hybrid organic-inorganic polysilsesquioxane prepared from 1,4-Bis-triethoxysilyl-benzene in ethanol.

12. A method of protecting a user against chemical warfare agents comprising: applying a topical skin protectant formulation for neutralizing chemical warfare agents into less toxic products comprising:
    a) a barrier cream; and
    b) one or more active moieties, said one or more active moieties comprising hybrid organic-inorganic polysilsesquioxanes.

13. A method of protecting a user against chemical warfare agents comprising:
    a) applying a first thin layer of solid active moiety powder comprising one or more hybrid organic-inorganic polysilsesquioxanes; and
    b) applying a second layer of a topical skin protectant formulation for neutralizing chemical warfare agents into less toxic products comprising a barrier cream and one or more active moieties comprising one or more hybrid organic-inorganic polysilsesquioxanes.

14. The method of claim 13, wherein said one or more active moieties in the topical skin protectant formulation and in the solid active moiety powder is an organic hybrid organic-inorganic polysilsesquioxane selected from the group consisting of
    a) hybrid organic-inorganic polysilsesquioxane prepared from 60% 1,4-Bis-triethoxysilyl-benzene and 40% 3-Triethoxysilyl-propane-1-thiol; and
    b) hybrid organic-inorganic polysilsesquioxane prepared from 40% 1,4-Bis-triethoxysilyl-benzene and 60% 3-Triethoxysilyl-propane-1-thiol;
    c) hybrid organic-inorganic polysilsesquioxane prepared from 20% 1,4-Bis-triethoxysilyl-benzene and 80% 3-Triethoxysilyl-propane-1-thiol;
    d) hybrid organic-inorganic polysilsesquioxane prepared from 60% 1,4-Bis-triethoxysilyl-benzene and 40% 1-Triethoxysilyl-3-(3-triethoxysilyl-propyldisulfanyl)-propane;
    e) hybrid organic-inorganic polysilsesquioxane prepared from 40% 1,4-Bis-triethoxysilyl-benzene and 60% 1-Triethoxysilyl-3-(3-triethoxysilyl-propyldisulfanyl)-propane;
    f) hybrid organic-inorganic polysilsesquioxane prepared from 20% 1,4-Bis-triethoxysilyl-benzene and 80% 1-Triethoxysilyl-3-(3-triethoxysilyl-propyldisulfanyl)-propane;

g) hybrid organic-inorganic polysilsesquioxane prepared from 1,4-Bis-triethoxysilyl-benzene in tetrahydrofuran; and h) hybrid organic-inorganic polysilsesquioxane prepared from 1,4-Bis-triethoxysilyl-benzene in ethanol.

15. A method of protecting a user against chemical warfare agents comprising:
   a) applying a first layer of a topical skin protectant formulation for neutralizing chemical warfare agents into less toxic products comprising a barrier cream and one or more active moieties, said one or more active moieties comprising one or more hybrid organic-inorganic polysilsesquioxanes; and
   b) applying a thin layer of solid active moiety powder over the first layer, said solid active moiety powder comprising one or more hybrid organic-inorganic polysilsesquioxanes.

16. The method of claim 15, wherein said one or more active moieties in the topical skin protectant formulation and in the solid active moiety powder is an hybrid organic-inorganic polysilsesquioxanes selected from the group consisting of
   a) hybrid organic-inorganic polysilsesquioxane prepared from 60% 1,4-Bis-triethoxysilyl-benzene and 40% 3-Triethoxysilyl-propane-1-thiol;
   b) hybrid organic-inorganic polysilsesquioxane prepared from 40% 1,4-Bis-triethoxysilyl-benzene and 60% 3-Triethoxysilyl-propane-1-thiol;
   c) hybrid organic-inorganic polysilsesquioxane prepared from 20% 1,4-Bis-triethoxysilyl-benzene and 80% 3-Triethoxysilyl-propane-1-thiol;
   d) hybrid organic-inorganic polysilsesquioxane prepared from 60% 1,4-Bis-triethoxysilyl-benzene and 40% 1-Triethoxysilyl-3-(3-triethoxysilyl-propyldisulfanyl)-propane;
   e) hybrid organic-inorganic polysilsesquioxane prepared from 40% 1,4-Bis-triethoxysilyl-benzene and 60% 1-Triethoxysilyl-3-(3-triethoxysilyl-propyldisulfanyl)-propane;
   f) hybrid organic-inorganic polysilsesquioxane prepared from 20% 1,4-Bis-triethoxysilyl-benzene and 80% 1-Triethoxysilyl-3-(3-triethoxysilyl-propyldisulfanyl)-propane;
   g) hybrid organic-inorganic polysilsesquioxane prepared from 1,4-Bis-triethoxysilyl-benzene in tetrahydrofuran; and
   h) hybrid organic-inorganic polysilsesquioxane prepared from 1,4-Bis-triethoxysilyl-benzene in ethanol.

17. A method of making a topical skin protectant formulation comprising:
   mixing
   a) one or more active moieties comprising hybrid organic-inorganic polysilsesquioxanes with
   b) a barrier cream comprising poly(tetrafluoroethylene) resins dispersed in perfluorinated polyether oils.

18. The method of claim 17, wherein said hybrid organic-inorganic polysilsesquioxanes are selected from the group consisting of
   a) hybrid organic-inorganic polysilsesquioxane prepared from 60% 1,4-Bis-triethoxysilyl-benzene and 40% 3-Triethoxysilyl-propane-1-thiol;
   b) hybrid organic-inorganic polysilsesquioxane prepared from 40% 1,4-Bis-triethoxysilyl-benzene and 60% 3-Triethoxysilyl-propane-1-thiol;
   c) hybrid organic-inorganic polysilsesquioxane prepared from 20% 1,4-Bis-triethoxysilyl-benzene and 80% 3-Triethoxysilyl-propane-1-thiol;
   d) hybrid organic-inorganic polysilsesquioxane prepared from 60% 1,4-Bis-triethoxysilyl-benzene and 40% 1-Triethoxysilyl-3-(3-triethoxysilyl-propyldisulfanyl)-propane;
   e) hybrid organic-inorganic polysilsesquioxane prepared from 40% 1,4-Bis-triethoxysilyl-benzene and 60% 1-Triethoxysilyl-3-(3-triethoxysilyl-propyldisulfanyl)-propane;
   f) hybrid organic-inorganic polysilsesquioxane prepared from 20% 1,4-Bis-triethoxysilyl-benzene and 80% 1-Triethoxysilyl-3-(3-triethoxysilyl-propyldisulfanyl)-propane;
   g) hybrid organic-inorganic polysilsesquioxane prepared from 1,4-Bis-triethoxysilyl-benzene in tetrahydrofuran; and
   h) hybrid organic-inorganic polysilsesquioxane prepared from 1,4-Bis-triethoxysilyl-benzene in ethanol.

19. A topical skin protectant formulation comprising: about 4% of hybrid organic-inorganic polysilsesquioxane prepared from 60% 1,4-Bis-triethoxysilyl-benzene and 40% 3-Triethoxysilyl-propane-1-thiol, and
   a) about 58% perfluoropolyether; and
   b) about 38% polytetrafluoroethylene.

20. A topical skin protectant formulation comprising:
   a) about 4% of hybrid organic-inorganic polysilsesquioxane prepared from 40% 1,4-Bis-triethoxysilyl-benzene and 60% 3-Triethoxysilyl-propane-1-thiol, and
   b) about 58% perfluoropolyether; and
   c) about 38%polytetrafluoroethylene.

21. A topical skin protectant formulation comprising:
   a) about 4% of hybrid organic-inorganic polysilsesquioxane prepared from 20% 1,4-Bis-triethoxysilyl-benzene and 80% 3-Triethoxysilyl-propane-1-thiol, and
   b) about 58% perfluoropolyether; and
   c) about 38% polytetrafluoroethylene.

22. A topical skin protectant formulation comprising:
   a) about 5% of hybrid organic-inorganic polysilsesquioxane prepared from 60% 1,4-Bis-triethoxysilyl-benzene and 40% 1-Triethoxysilyl-3-(3-triethoxysilyl-propyldisulfanyl).-propane;
   b) about 7% perfluoropolyether; and
   c) about 38% polytetrafluoroethylene.

23. A topical skin protectant formulation comprising:
   a) about 4% of hybrid organic-inorganic polysilsesquioxane prepared from 40% 1,4-Bis-triethoxysilyl-benzene and 60% 1-Triethoxysilyl-3-(3-triethoxysilyl-propyldisulfanyl).-propane;
   b) about 58% perfluoropolyether; and
   c) about 38% polytetrafluoroethylene.

24. A topical skin protectant formulation comprising:
   a) about 4% of hybrid organic-inorganic polysilsesquioxane prepared from 20% 1,4-Bis-triethoxysilyl-benzene and 80% 1-Triethoxysilyl-3-(3-triethoxysilyl-propyldisulfanyl).-propane;
   b) about 58% perfluoropolyether; and
   c) about 38% polytetrafluoroethylene.

25. A topical skin protectant formulation comprising:
   a) about 3% of hybrid organic-inorganic polysilsesquioxane prepared from 60% 1,4-Bis-triethoxysilyl-benzene and 40% 3-Triethoxysilyl-propane-1-thiol
   b) about 57% perfluoropolyether; and
   c) about 40% polytetrafluoroethylene.

26. A topical skin protectant formulation comprising:
a) about 4% of hybrid organic-inorganic polysilsesquioxane prepared from 60% 1,4-Bis-triethoxysilyl-benzene and 40% 3-Triethoxysilyl-propane-1-thiol, and
b) about 96% perfluoropolyether.

27. A topical skin protectant formulation comprising:
a) about 5% of hybrid organic-inorganic polysilsesquioxane prepared from 1,4-Bis-triethoxysilyl-benzene in EtOH;
b) about 51% perfluoropolyether; and
c) about 44% polytetrafluoroethylene.

28. A topical skin protectant formulation comprising:
a) about 1% of Hybrid organic-inorganic polysilsesquioxane prepared from 60% 1,4-Bis-triethoxysilyl-benzene and 40% 1-Triethoxysilyl-3-(3-triethoxysilyl-propyldisulfanyl).-propane
b) about 50% perfluoropolyether; and
c) about 49% polytetrafluoroethylene.

29. A topical skin protectant formulation comprising:
a) about 1% of hybrid organic-inorganic polysilsesquioxane prepared from 40% 1,4-Bis-triethoxysilyl-benzene and 60% 1-Triethoxysilyl-3-(3-triethoxysilyl-propyldisulfanyl).-propnae;
b) about 50% perfluoropolyether; and
c) about 49%polytetrafluoroethylene.

30. A topical skin protectant formulation comprising:
a) about 1% of hybrid organic-inorganic polysilsesquioxane prepared from 20% 1,4-Bis-triethoxysilyl-benzene and 80% 1-Triethoxysilyl-3-(3-triethoxysilyl-propyldisulfanyl)-propane;
b) about 50% perfluoropolyether; and
c) about 49% polytetrafluoroethylene.

31. A topical skin protectant formulation comprising:
a) about 2.5% of Silica Gel;
b) about 50% perfluoropolyether; and
c) about 47% polytetrafluoroethylene.

32. A topical skin protectant formulation comprising:
a) about 5% of hybrid organic-inorganic polysilsesquioxane prepared from 1,4-Bis-triethoxysilyl-benzene polymerized in tetrahydrofuran;
b) about 51% perfluoropolyether; and
c) about 44% polytetrafluoroethylene.

33. A topical skin protectant formulation comprising:
a) about 5% of hybrid organic-inorganic polysilsesquioxane prepared from 1,4-Bis-triethoxysilyl-benzene polymerized in ethanol;
b) about 51% perfluoropolyether; and
c) about 44% polytetrafluoroethylene.

34. A topical skin protectant formulation comprising:
a) about 5% of 60% 1,4-Bis-triethoxysilyl-benzene and 40% 3-Triethoxysilyl-propane-1-thiol;
b) about 51% perfluoropolyether; and
c) about 44% polytetrafluoroethylene.

35. A topical skin protectant formulation comprising:
a) about 5% of 60% 1,4-Bis-triethoxysilyl-benzene and 40% 3-Triethoxysilyl-propane-1-thiol;
b) about 51% perfluoropolyether; and
c) about 44% polytetrafluoroethylene.

36. A topical skin protectant formulation comprising:
a) about 5% of 60% 1,4-Bis-triethoxysilyl-benzene and 40% 3-Triethoxysilyl-propane-1-thiol;
b) about 51% perfluoropolyether; and
c) about 44% polytetrafluoroethylene.

37. A topical skin protectant formulation for neutralizing chemical warfare agents into less toxic products comprising:
a) a barrier base cream, said barrier base cream comprising of about 30–50% poly(tetrafluoroethylene) resins dispersed in 40–60% perfluorinated polyether oils;
b) one or more active moieties comprising one or more hybrid organic-inorganic polysilsesquioxanes selected from the group consisting of
i. hybrid organic-inorganic polysilsesquioxane prepared from 60% 1,4-Bis-triethoxysilyl-benzene and 40% 3-Triethoxysilyl-propane-1-thiol;
ii. hybrid organic-inorganic polysilsesquioxane prepared from 40% 1,4-Bis-triethoxysilyl-benzene and 60% 3-Triethoxysilyl-propane-1-thiol;
iii. hybrid organic-inorganic polysilsesquioxane prepared from 20% 1,4-Bis-triethoxysilyl-benzene and 80% 3-Triethoxysilyl-propane-1-thiol;
iv. hybrid organic-inorganic polysilsesquioxane prepared from 60% 1,4-Bis-triethoxysilyl-benzene and 40% 1-Triethoxysilyl-3-(3-triethoxysilyl-propyldisulfanyl)-propane;
v. hybrid organic-inorganic polysilsesquioxane prepared from 40% 1,4-Bis-triethoxysilyl-benzene and 60% 1-Triethoxysilyl-3-(3-triethoxysilyl-propyldisulfanyl)-propane;
vi. hybrid organic-inorganic polysilsesquioxane prepared from 20% 1,4-Bis-triethoxysilyl-benzene and 80% 1-Triethoxysilyl-3-(3-triethoxysilyl-propyldisulfanyl)-propane;
vii. hybrid organic-inorganic polysilsesquioxane prepared from 1,4-Bis-triethoxysilyl-benzene in tetrahydrofuran;
viii. hybrid organic-inorganic polysilsesquioxane prepared from 1,4-Bis-triethoxysilyl-benzene in ethanol; and
ix. one or more additives consisting of water, surfactants, stabilizers, camouflage paints, and sunscreens.

38. A topical skin protectant formulation for neutralizing chemical warfare agents into less toxic products comprising one or more active moieties, wherein said active moiety is one or more hybrid organic-inorganic polysilsesquioxanes.

39. The topical skin protectant formulation of claim 38, further comprising a base cream.

40. The topical skin protectant formulation of claim 2, wherein the amount of active moiety is about 1–20%; the amount of perfluorinated polyether oil is about 40 to 60%, and the amount of poly(tetrafluoroethylene) is about 30 to 50%.

41. The topical skin protectant formulation of claim 1, wherein said chemical warfare agents are one or more of the group consisting of blistering agents, G class nerve agents, and VX.

42. The topical skin protectant formulation of claim 41, wherein said blistering agent is sulfur mustard.

43. The topical skin protectant formulation of claim 41, wherein said G class nerve agent is soman.

\* \* \* \* \*